United States Patent [19]

Sawa et al.

[11] 4,293,690
[45] Oct. 6, 1981

[54] PRODUCTION OF 2,6-DIAMINONEBULARINES

[75] Inventors: Yoichi Sawa, Sengokuhigashimachi; Yoshiyuki Kawakami, Tsurumaihigashi; Ryuji Marumoto, Osaka, all of Japan

[73] Assignee: Takeda Chemical Industries, Ltd., Osaka, Japan

[21] Appl. No.: 136,072

[22] Filed: Mar. 28, 1980

[30] Foreign Application Priority Data

Apr. 2, 1979 [JP] Japan .................. 54-39562

[51] Int. Cl.³ .................. C07H 19/16; C07H 19/18
[52] U.S. Cl. .................. 536/24; 536/23; 536/25
[58] Field of Search .............. 536/24, 26, 23; 544/262

[56] References Cited

U.S. PATENT DOCUMENTS

| | | | |
|---|---|---|---|
| 3,134,778 | 5/1964 | Weinstock et al. | 544/262 |
| 3,826,803 | 7/1974 | Tolman et al. | 536/26 |
| 3,857,842 | 12/1974 | Asai | 260/252 |
| 3,936,439 | 2/1976 | Marumoto et al. | 536/24 |
| 4,056,674 | 11/1977 | Robins et al. | 536/24 |

Primary Examiner—Johnnie R. Brown
Attorney, Agent, or Firm—Wenderoth, Lind & Ponack

[57] ABSTRACT

Compounds of the formula

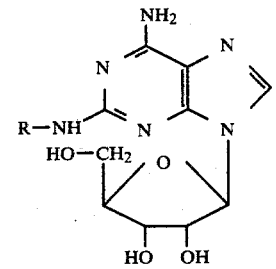

wherein
R is phenyl which may be substituted; or their acid addition salts, are produced in good yield by reacting a compound of the formula

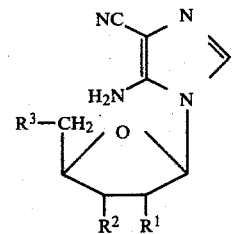

wherein $R^1$, $R^2$ and $R^3$, independently of one another, are hydroxyl which may be protected, which is prepared in 2 or 3 steps from 5-amino-1-β-D-ribofuranosylimidazole-4-carboxamide, with a compound of the formula

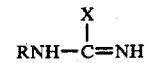

wherein R has the same meaning as defined above and X is amino which may be substituted or lower alkylthio, and, if necessary subjecting the resulting compound to a treatment for removal of protective groups on its hydroxyls.

16 Claims, No Drawings

PRODUCTION OF 2,6-DIAMINONEBULARINES

The present invention relates to a novel and improved method for producing 2,6-diaminonebularines. More particularly, the present invention relates to a commercially profitable method for producing $N^2$-substituted 2,6-diaminonebularines of the formula

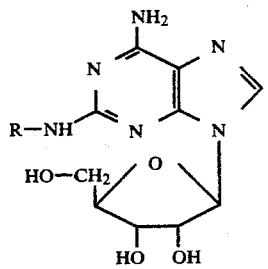

wherein R is phenyl which may be substituted; or their acid addition salts.

The above-mentioned compounds (I) and their salts have excellent coronary actions as a vasodilator and a platelet aggregation inhibitor and, as such, are of value as coronary vasodilators, platelet aggregation inhibitors, and the like. (Refer to U.S. Pat. No. 3,936,439 issued on Feb. 3, 1976). Among hitherto-known processes for the production of the above-mentioned compounds (I) are mentioned a process comprising reacting a 2-halogeno-adenosine with an amine of the formula R—NH$_2$ wherein R has the same meaning as defined hereinbefore, and the process comprising the steps of reacting a 2-halogeno-inosine with the above-mentioned amine, to prepare a 2-substituted aminoinosine, replacing the 6-hydroxyl group thereof with a reactive group (e.g. halogen, mercapto or alkylthio) and subjecting the same to ammonolysis (refer to the U.S. patent mentioned above). However, these known processes invariably require at least six reaction steps from the starting material 5-amino-1-β-D-ribofuranosylimidazole-4-carboxamide (hereinafter referred to briefly as AICAr, which is a fermentation product, to the final compound (I) and give the compound (I) only in unsatisfactory yields. Moreover, these processes have such a disadvantage as involving the use of intermediates which are not easy to handle.

Under the above-mentioned technical situation, the present inventors carried out extensive research to develop a more industrially profitable method for producing the compound (I), and have unexpectedly found that the compound (I) can be produced in good yield by reacting a compound of the formula

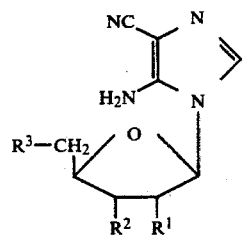

wherein $R^1$, $R^2$ and $R^3$, independently of one another, are hydroxyl which may be protected, which is easy to handle and can be prepared in good yield via 2 or 3 steps from AICAr, with a compound of the formula

wherein R has the same meaning as defined above and X is amino which may be substituted or lower alkylthio, and if necessary, subjecting the resulting compound to a treatment for removal of protective groups on its hydroxyls. This finding was followed by further research which has culminated in the establishment of the present invention.

Thus, in accordance with the first aspect of the present invention, this invention provides a method for producing the compounds (I) in good yield, which comprises reacting a compound (II) with a compound (III) and, if necessary, subjecting the resulting compound to a treatment for removal of the protective groups.

In accordance with the second aspect, the present invention provides a method for producing the compound (I) in good yield in 3 or 4 steps by way of the compound (II) from AICAr.

Referring to the formula (II), protective groups on protected hydroxyls for $R^1$, $R^2$ and $R^3$ may, for example, be carboxylic acid-derived acyl groups which may be aliphatic, aromatic, heterocyclic, saturated or unsaturated and which may be exemplified by acetyl, propionyl, caproyl, benzoyl, toluoyl, furoyl, etc.; alkoxycarbonyl groups such as methoxycarbonyl, butoxycarbonyl and the like, nitro group, sulfonyl group, isopropylidene group, alkoxyalkylidene group, etc. Among them, an acyl group of a carboxylic acid having 4 or less carbon atoms or an aromatic carboxylic acid having 7 to 8 carbon atoms is preferably employed and, in particular, propionyl is most preferred. All of $R^1$, $R^2$ and $R^3$ can be protected hydroxyls or partially protected hydroxyls, for example, only $R^2$ and $R^3$ are protected, or all of $R^1$, $R^2$ and $R^3$ can be non-protected hydroxyls. The protective groups of these protected hydroxyls are generally cleaved in the reaction of the compound (II) with the compound (III), but, if necessary, they can be easily removed by a conventional procedure, for example, treatment with a base such as aqueous ammonia, an alkali metal and the like when the protective group is acyl, catalytic reduction when the protective group is nitro, or treatment with an acid such as formic acid, acetic acid, hydrochloric acid and the like when the protective group is isopropylidene.

The phenyl group represented by R in the formula (III) can be substituted with halogen(s), lower alkyl(s), lower alkoxyl(s), carbamoyl(s) which may be substituted or lower alkanoyl(s). Examples of halogen are chlorine, bromine, fluorine, etc. The lower alkyl can be a straight-chain or branched alkyl group, for example, methyl, ethyl, isopropyl, t-butyl, hexyl, etc. and, in particular, those having 4 or less carbon atoms are preferred. The lower alkoxyl can be a straight-chain or branched alkoxyl, for example, methoxy, t-butoxy, hexoxy, etc. and, in particular, those having 4 or less carbon atoms are preferred. Examples of carbamoyl which may be substituted are lower alkylsubstituted carbamoyl, for example, methylcarbamoyl, dimethylcarbamoyl, ethylcarbamoyl, butylcarbamoyl and the like, aromatic hydrocarbon-substituted carbamoyl, for example, phenylcarbamoyl and the like, as well as morpholinocarbonyl, piperidinocarbonyl, etc. Examples of alkyl in lower alkanoyl are the same as mentioned in lower alkyl. The phenyl group may have one or more substituents described above at optional positions on the ring.

The substitutent X in the formula (III) represents amino which may be substituted or lower alkylthio, and the substituent on the amino group is preferably the same group as R, but may be different from R. The lower alkyl moiety of lower alkylthio is advantageously one having 4 or less carbon atoms such as, for example, methyl, ethyl, isopropyl, butyl, t-butyl and the like.

The compounds represented by the formula (III), for example, diphenylguanidines which may be substituted, can be easily obtained by the process described in, for example, "Berichte der Deutchen Chemischen Gesellschaft", Vol.2, p460 (1869) or a process similar thereto; phenylguanidines which may be substituted can be easily obtained by the process described in, for example, "Journal of the American Chemical Society", Vol.51, p477 (1929) or a process similar thereto; and phenyl S-alkylisothioureas can be easily obtained by the process described in, for example, "Berichte der Deutchen Chemischen Gesellschaft", Vol.14, p1489 (1881) or a process similar thereto.

In reacting a compound (II) with a compound (III) in accordance with this invention, the compound (III) is generally used in an amount of at least an equimolar amount, preferably, about 1.2 to 5 moles, per mole of the compound (II). Generally, the reaction is advantageously carried out in the presence of aniline or a derivative thereof represented by the formula:

RNH$_2$                                          (IV)

wherein R is as defined above.

This reaction proceeds smoothly in the presence of aniline or a derivative thereof, although addition thereof is not essential. The reaction can be carried out in the presence of a solvent, and the solvent may be any type of organic solvent which does not adversely affect the reaction. Examples of solvents which can be advantageously used are alkanols (butanol, hexanol, octanol, etc.), dioxane, dimethylformamide, dimethylacetamide, dimethylsulfoxide, ethylene glycols (ethylene glycol, ethylene glycol diethyl ether, ethylene glycol monomethyl ether, diethylene glycol monomethyl ether, diethylene glycol, diethylene glycol dimethyl ether, etc.), secondary or tertiary amines including cyclic amines, for example, diethanolamine, triethylamine, pyridine, N-methylpyrrolidone, morpholine, piperidine, etc.) or a mixture of these solvents. When such a solvent is used, it can be used in an amount of 1 to 50 times (w/v), preferably 5 to 15 times (w/v), relative to the amount of the compound (II). Generally, the reaction proceeds under heating at about 50° C. to 250° C., advantageously at about 100° C. to 200° C., and preferably at 120° C. to 180° C. Also, the reaction may be effected at superatmospheric pressure, but is advantageously conducted at atmospheric pressure.

When the compound thus produced still has protective groups on its hydroxyl groups, the compound is then subjected to a treatment for removal of the protective groups as described above whereby the desired compound (I) can be easily obtained.

The starting compound (II) described above can be produced in high yield from the above AICAr in two or three steps. Accordingly, the invention of this application provides a process for producing the compound (I) in high yield in three or four steps from AICAr via the compound (II) which is easily handled, that is, a process characterized by protecting hydroxyls of AICAr followed by dehydration reaction, reacting the resulting compound represented by the formula

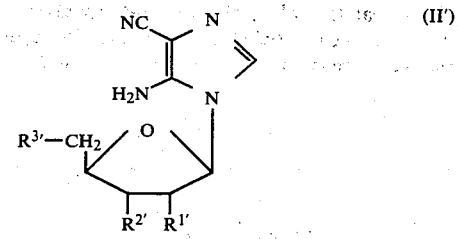

wherein R$^{1'}$, R$^{2'}$ and R$^{3'}$ each represent protected hydroxyl, with or without removing the protective groups, with a compound represented by the formula (III) and optionally removing the protective groups from the resulting compound.

In the process of this invention, the step for protecting the hydroxyls of AICAr is effected by reacting AICAr with a compound corresponding to the protective groups of hydroxyls represented by R$^{1'}$, R$^{2'}$ and R$^{3'}$ (wherein the protective groups are the same as those described hereinbefore for R$^1$, R$^2$ and R$^3$), the example, a reactive derivative of carboxylic acid or sulfonic acid, nitric acid, a ketone, an aldehyde, ortho ester and the like. The carboxylic acid used in the above reaction can be an aliphatic, aromatic or heterocyclic carboxylic acid such as acetic acid, propionic acid, caproic acid, benzoic acid, toluic acid, furancarboxylic acid and the like. These carboxylic acids are generally used as reactive derivatives thereof in the carboxyl function, for example, a halide such as a chloride, a bromide, etc. or an acid anhydride, etc. These carboxylic acid reactive derivatives are advantageously used in an amount of about 3 moles or more, preferably about 3 to 15 moles, per mole of AICAr. The reaction of AICAr with the above carboxylic acid derivative is preferably conducted in the presence of a solvent which may be any type of solvent so long as it does not adversely affect the reaction. For example, an aromatic hydrocarbon solvent such as benzene, toluene, xylene and the like, a halogenated hydrocarbon solvent such as dichloromethane, chloroform and the like, an organic base such as pyridine, triethylamine and the like, or an acidic solvent such as the above carboxylic acid per se, etc. can be preferably used. The reaction generally proceeds smoothly at room temperature, but the reaction rate may be adjusted by heating or cooling the reaction system, if desired.

The reaction of AICAr with a nitric acid, for example, fuming nitric acid, is carried out at a temperature of from −30° C. to 20° C., preferably 0° C. to 20° C. Fuming nitric acid is preferably used in a large excess amount.

The reaction of AICAr with a sulfonic acid derivative, for example, a sulfonyl chloride such as methanesulfonyl chloride, toluenesulfonyl chloride can be generally carried out using 3 to 10 moles of a sulfonyl chloride per mole of AICAr, preferably in the presence of an organic solvent, for example, pyridine, etc. The reaction temperature is preferably in the range of 10° C. to 30° C.

The reaction of AICAr with an aldehyde, a ketone or an ortho ester is carried out by reacting AICAr with a large excess, preferably about 10 to 100 moles, per mole of AICAr, of the aldehyde, ketone or ortho ester, preferably in the presence of an acid catalyst such as a mineral acid (hydrochloric acid, sulfuric acid, phosphoric acid, etc.), a Lewis acid (zinc chloride, aluminum chloride, etc.), toluenesulfonic acid and the like. In this reaction, a solvent which does not adversely affect the reaction, for example, an organic solvent such as dimethylformamide, dimethylacetamide, dioxane, ether (for example, diethyl ether, etc.) and the like can be used, if necessary. The reaction temperature preferably ranges from about 0° C. to about 30° C.

Among the thus produced AICAr in which the hydroxyls are protected, 5-amino-1-(2,3,5-tri-O-propionyl-$\beta$-D-ribofuranosyl)imidazole-4-carboxamide is a novel compound which has never been disclosed in literature and, since this compound can be obtained as crystals having a relatively high melting point, it can be used most advantageously in the process of this invention.

The process of this invention comprises converting the hydroxyl-protected AICAr obtained as described above into the compound (II') by dehydration reaction. The dehydration reaction can be attained by any procedure so long as it is capable of converting the carboxamide at the 4-position of AICAr into a carbonitrile, and is preferably conducted by using a dehydrating agent in the presence of an organic base. Examples of the dehydrating agent are phosphorus halides (phosphorus oxychloride, phosphorus trichloride, phosphorus pentachloride, etc.), acid chlorides (for example, acetyl chloride, benzoyl chloride, thionyl chloride, p-toluenesulfonyl chloride, methanesulfonyl chloride, carbobenzoxy chloride, etc.) and the like. These dehydrating agents can be preferably used in at least an equivalent amount with respect to AICAr. preferably, about 0.8 to about 3 moles per mole of AICAr. Examples of the organic bases are trimethylamine, triethylamine, tri-n-butylamine, picoline, collidine, lutidine, pyridine and the like, and these bases can be used in at least an equimolar amount with respect to the hydroxyl-protected AICAr, preferably about 3 to about 10 moles per mole of the AICAr. Generally, the reaction is preferably conducted in the presence of a solvent, and solvents such as chloroform, dichloromethane, tetrahydrofuran, dioxane, etc. can be used advantageously. The reaction proceeds rapidly at room temperature, but heating or cooling at a temperature ranging from about 0° C. to about 50° C. may be applied in order to adjust the reaction rate. The compound (II') thus obtained can then be subjected, with or without having been subjected previously to the treatment for removing protective groups, to the cyclization reaction (reaction with the compound (III)) as described above, and the resulting compound is subjected to the above treatment for removing protective groups, if such protective groups remain in the compound, whereby the desired compound (I) can be produced.

The $N^2$-substituted 2,6-diaminonebularine (I) thus produced can be easily isolated from the reaction solution by a procedure which is well known in the art. For example, the compound (I) can be purified by distilling off any excess of the base and the solvent from the reaction mixture, washing the residue with a solvent such as lower alkanol and then recrystallizing from water, lower alkanol, dimethylformamide or a mixture thereof. The compound of the formula (I) can be obtained in the form of a salt, for example, a physiologically acceptable acid addition salt such as a salt with a mineral acid (hydrochloric acid salt, sulfuric acid salt, etc.).

The process in accordance with the present invention has the following advantages.

(1) The desired compound can be produced in high yield.

(2) The process comprises fewer reaction steps as compared with conventional processes.

(3) The process does not require a high pressure vessel, etc. since the retention can be conducted at atmospheric pressure.

(4) The process does not require, in particular, a catalyst, etc. since the reaction can be conducted under neutral to weakly alkaline condition.

(5) The formation of by-products is sparse and the desired product can be easily isolated.

The process of the present invention is further illustrated in greater detail by the following Examples, but they are not to be construed as limiting the present invention.

EXAMPLE 1

140 ml of aniline was added to 16.3 g of 5-amino-1-(2,3,5-tri-O-propionyl-$\beta$-D-ribofuranosyl)imidazole-4-carbonitrile, and the mixture was heated to 140° C. in a nitrogen stream. 17.0 g of 1,3-diphenylguanidine was added thereto in portions and, after heating the mixture at 140°–150° C. for 7 hours, aniline was distilled off and 250 ml of ethanol was added to the residue. After cooling, the precipitated crystals were collected by filteration and recrystallized from aqueous butanol and then from water to obtain 7.8 g of $N^2$-phenyl-2,6-diaminonebularine. Yield, 54.9%. Melting point, 246°–247° C.

Elemental Analysis: Calcd for $C_{16}H_{18}N_6O_4$: C, 53.62; H, 5.06; N, 24.45(%). Found: C, 53.58; H, 5.00; N, 23.40(%).

EXAMPLE 2

A mixture of 8.1 g of 5-amino-1-(2,3,5-tri-O-propionyl-$\beta$-D-ribofuranosyl)imidazole-4-carbonitrile, 70 ml of aniline and 5 g of sodium bicarbonate was heated at 140° C. and 10 g of 1,3-diphenylguanidine was added thereto in portions. After heating the mixture for 5 hours, the reaction mixture was worked up in the same manner as described in Example 1 to obtain 4.2 g of $N^2$-phenyl-2,6-diaminonebularine as colorless needles. Yield, 59.2%. Melting point, 246°–247° C.

Elemental Analysis: Calcd for $C_{16}H_{18}N_6O_4$: C, 53.62; H, 5.06; N, 23.45(%). Found: C, 53.60; H, 5.00; N, 23.53(%).

EXAMPLE 3

To a stirred mixture of 50 g of 5-amino-1-$\beta$-D-ribofuranosylimidazole-4-carbonitrile and 500 ml of aniline was added 90 g of 1,3-diphenylguanidine in portions at 150° to 155° C. in a nitrogen stream. After stirring for 5 hours under heating, aniline was distilled off. 250 ml of ethanol was added to the residue followed by cooling, and the precipitated crystals were collected by filteration. The crystals were recrystallized from aqueous butanol and then from water to obtain 51.3 g of $N^2$-phenyl-2,6-diaminonebularine as colorless needles. Yield, 68.8%. Melting point, 245°–247° C.

Elemental Analysis: Calcd for $C_{16}H_{18}N_6O_4$: C, 53.62; H, 5.06; N, 23.45(%). Found: C, 53.58; H, 4.96; N, 23.28(%).

EXAMPLE 4

A mixture of 50 g of 5-amino-1-$\beta$-D-ribofuranosylimidazole-4-carbonitrile, 300 ml of diethylene glycol monomethyl ether and 100 g of b 1,3-diphenylguanidine was stirred at 150° C. in a nitrogen stream for 7 hours. The solvent was distilled off and 400 ml of ethanol was added to the residue, followed by cooling. The precipitated crystals were filtered and recrystallized from aqueous butanol and then from water to obtain 31 g of $N^2$-phenyl-2,6-diaminonebularine as colorless needles. Yield, 41.6%. Melting point, 245°–247° C.

Elemental Analysis: Calcd for $C_{16}H_{18}N_6O_4$: C, 53.62; H, 5.06; N, 23.45(%). Found: C, 53.54; H, 5.02; N, 23.36(%).

EXAMPLE 5

13.1 g of S-methyl-N-phenylisothiourea was added in portions to a stirring mixture of 6 g of 5-amino-1-$\beta$-D-ribofuranosylimidazole-4-carbonitrile and 60 ml of aniline at 160° C. in a nitrogen stream, followed by allowing the mixture to react for 11 hours. Aniline was then distilled off and ethanol was added to the mixture, followed by cooling. The precipitated crystals were collected by filtration and the resulting crude crystals were recrystallized from aqueous butanol and then from water to obtain 2.5 g of $N^2$-phenyl-2,6-diaminonebularine as colorless needles. Yield, 28.0%. Melting point, 246°–247° C.

Elemental Analysis: Calcd for $C_{16}H_{18}N_6O_4$: C, 53.62; H, 5.06; N, 23.45(%). Found: C, 53.49; H, 5.15; N, 23.18(%).

EXAMPLE 6

A mixture of 5 g of 5-amino-1-(2,3,5-tri-O-propionyl-$\beta$-D-ribofuranosyl)imidazole-4-carbonitrile, 50 ml of aniline and 3.4 g of phenyl guanidine carbonate was stirred at 130° C. in a nitrogen stream for 10 hours. The reaction solution was concentrated, to which were added methanol and ammonia water. After stirring at room temperature for 7 hours, the mixture was concentrated, and ethanol was added thereto, followed by cooling. The precipitated crystals were collected by filtration and recrystallized from water to obtain 2.2 g of $N^2$-phenyl-2,6-diaminonebularine as colorless needles. Yield, 50.1%. Melting point, 246°–247° C.

Elemental Analysis: Calcd for $C_{16}H_{18}N_6O_4$: C, 53.62; H, 5.06; N, 23.45(%). Found: C, 53.51; H, 5.01; N, 23.38(%).

EXAMPLE 7

(I) A mixture of 1.5 kg of 5-amino-1-$\beta$-D-ribofuranosylimidazole-4-carboxamide, 2.93 l of pyridine and 2.33 l of propionic anhydride was stirred at room temperature for 10 hours. The reaction mixture was concentrated under reduced pressure and 10 l of water was added thereto, followed by cooling. The precipitated crystals were collected by filtration, washed with water and dried to obtain 2.27 kg of 5-amino-1-(2,3,5-tri-O-propionyl-$\beta$-D-ribofuranosyl)imidazole-4-carboxamide. Melting point, 115°–116° C. A portion of the product was recrystallized from ethanol-diethyl ether to obtain the above compound as colorless needles. Melting point, 117°–118° C.

Elemental Analysis: Calcd for $C_{18}H_{26}N_4O_8$: C, 50.70; H, 6.15; N, 13.14(%). Found: C, 50.62; H, 6.04; N, 13.18(%).

(II) A solution of 840 g of 5-amino-1-(2,3,5-tri-O-propionyl-$\beta$-D-ribofuranosyl)imidazole-4-carboxamide, 5.4 l of dichloromethane and 1.38 l of triethylamine was cooled to 0° C. or less, and a solution of 196 ml of phosphorus oxychloride in dichloromethane (1.8 l) was added dropwise thereto while maintaining the temperature below 0° C. After stirring for 1.5 hours, 2 l of water was added to the mixture below 0° C. and the dichloromethane layer was separated. The dichloromethane layer was washed successively with 2 l each of water, twice with 2 l of 1 N hydrochloric acid, and twice with 2 l each of a saturated aqueous sodium chloride solution, and then concentrated to dryness under reduced pressure to obtain 5-amino-1-(2,3,5-tri-O-propionyl-$\beta$-D-ribofuranosyl)imidazole-4-carbonitrile as a yellow brown viscous syrup.

To the above viscous syrup were added 1.6 l of methanol and 1.6 l of ammonia water to dissolve the substance, and the solution was stirred at room temperature for 5 hours. The reaction mixture was concentrated to dryness and the residue was cooled overnight with ice to obtain 264 g of 5-amino-1-$\beta$-D-ribofuranosylimidazole-4-carbonitrile as gray-white needles. Melting point, 206°–208° C.

Elemental Analysis: Calcd for $C_9H_{12}N_4O_4$: C, 45.00; H, 5.04; N, 23.32(%). Found: C, 45.12; H, 5.08; N, 23.40(%).

(III) 24.8 g of phenyl guanidine carbonate was added in portions to a stirring mixture of 20 g of 5-amino-1-$\beta$-D-ribofuranosylimidazole-4-carbonitrile and 200 ml of aniline at 130° C. in a nitrogen stream, followed by allowing the mixture to react for 5 hours. Aniline was distilled off, and 300 ml of ethanol was added to the residue. The precipitated crystals were filtered and recrystallized from water to obtain 21.6 g of $N^2$-phenyl-2,6-diaminonebularine as colorless needles. Yield, 72.3%. Melting point 246°–247° C.

Elemental Analysis: Calcd for $C_{16}H_{18}N_6O_4$: C, 53.62; H, 5.06; N, 23.45(%). Found: C, 53.41; H, 4.88; N, 23.44(%).

EXAMPLES 8 TO 17

4-Amino-1-$\beta$-D-ribofuranosylimidazole-4-carbonitrile was reacted with a compound of the formula

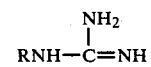

wherein R is defined in Table below, in the same manner as described in Example 7 (III) to obtain the $N^2$-substituted 2,6-diaminonebularines (I) shown in Table below.

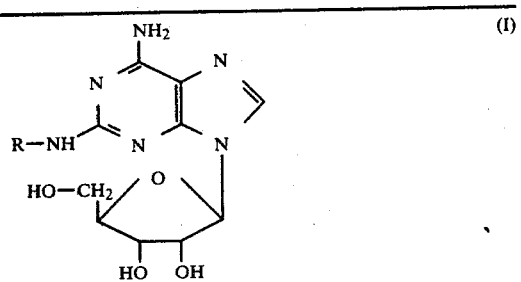

(I)

| Example No. | R | Molecular formula | Melting point(°C.) | Yield (%) |
|---|---|---|---|---|
| 8 | 4-H₃C-C₆H₄- | C₁₇H₂₀N₆O₄ · ½ H₂O | 193–195 | 61 |
| 9 | 3-H₃C-C₆H₄- | C₁₇H₂₀N₆O₄ | 231–232 | 53 |
| 10 | 4-H₃CO-C₆H₄- | C₁₇H₂₀N₆O₅ | 133–135 | 63 |
| 11 | 4-H₅C₂O-C₆H₄- | C₁₈H₂₂N₆O₅ | 177 | 58 |
| 12 | 2-Cl-4-H₃C-C₆H₃- | C₁₇H₁₉ClN₆O₄ | 250–251 | 51 |
| 13 | 4-H₂NCO-C₆H₄- | C₁₇H₁₉N₇O₅ | 277–279 | 52 |
| 14 | 3-H₂NCO-C₆H₄- | C₁₇H₁₉N₇O₅ | 190–192 | 62 |
| 15 | 4-(cyclohexyl-NHCO)-C₆H₄- | C₂₃H₂₉N₇O₅ | 267–268 | 54 |
| 16 | 4-H₃CCO-C₆H₄- | C₁₈H₂₀N₆O₅ | 142–143 | 58 |
| 17 | 2-H₃CCO-5-H₅C₂O-C₆H₃- | C₂₀H₂₄N₆O₆ · ½ H₂O | 128–129 | 52 |

EXAMPLE 18

30 ml of 4-ethoxyaniline and 30 ml of diethylene glycol monomethyl ether were added to 6 g of 5-amino-1-β-ribofuranosylimidazole-4-carbonitrile, and 12 g of 4-ethoxyphenylguanidine carbonate was added in portions to the mixture at 150° C. while stirring in a nitrogen stream. After heating the mixture for 3 hours, the solvent was distilled off and ethanol was added to the residue, followed by cooling. The precipitated crystals were collected by filteration and recrystallized from a dilute alcohol to obtain 5.5 g of N²-(4-ethoxyphenyl)-2,6-diaminonebularine as almost colorless needles. Yield, 55%. Melting point 177° C.

Elemental Analysis: Calcd for $C_{18}H_{22}N_6O_5$: C, 53.72; H, 5.51; N, 20.09(%). Found: C, 53.63; H, 5.27; N, 20.38(%).

EXAMPLE 19

To a stirred mixture of 20.0 g of 5-amino-1-β-D-ribofuranosylimidazole-4-carbonitrile in aniline (200 ml) was added 15.8 g of phenylguanidine at 130° C. in a nitrogen stream. After heating the mixture for 3.5 hours the solvent was evaporated off and water was added to the residue. The precipitate were collected by filteration and recrystallized from ethanol then from water to obtain 23.0 g of N²-phenyl-2,6-diaminonebularine as colorless needles. Yield, 80.4%.

Melting point 246°–247° C.

Elemental Analysis: Calcd. for $C_{16}H_{18}N_6O_4$: C, 53.62; H, 5.06; N, 23.45(%). Found: C, 53.40; H, 4.94; N, 23.22(%).

EXAMPLE 20

20.0 g of 5-amino-1-(2,3,5-tri-O-propyonyl-β-D-ribofuranosyl)imidazole-4-carbonitrile and 15.8 g of phenylguanidine were reacted in the same manner as described in Example 19 to obtain 10.6 g of N²-phenyl-2,6-diaminonebulamine as colorless needles. Yield, 62.9%. Melting point 246°–247° C.

Elemental Analysis: Calcd for $C_{16}H_{18}N_6O_4$: C, 53.62; H, 5.06; N, 23.45(%). Found: C, 53.36; H, 4.98; N, 23.34(%).

EXAMPLE 21

125 g of phenylguanidine carbonate was added in portions with stirring to a mixture of 100 g of 5-amino-1-β-D-ribofuranosylimidazole-4-carbonitrile and 1000 ml of aniline at 130° for 6 hours in stream of nitrogen. The reaction mixture was concentrated in vacuo. The residue was refluxed with 1300 ml of water for one hour. After cooling the precipitated crystals were collected by filteration. The crystals were refluxed with 1300 ml of ethanol for one hour. After cooling the obtained crystals were recrystallized from water to give $N^2$-2,6-diaminonebularine. Yield, 83.8%. Melting point 246°–247° C.

What is claimed is:

1. A method for producing a compound of the formula

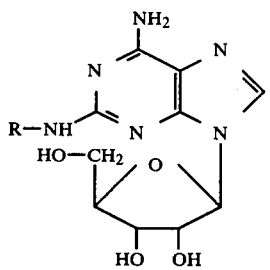

wherein
R is phenyl or phenyl substituted on the ring by halogen, $C_{1-4}$ alkyl, $C_{1-4}$ alkoxy, carbamoyl, lower alkyl carbamoyl, phenylcarbamoyl, morpholinocarbamoyl, piperidinocarbamoyl or $C_{2-5}$ alkanoyl; or an acid addition salt thereof, which consists of reacting a compound of the formula

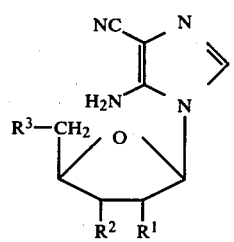

wherein
$R^1$, $R^2$ and $R^3$, independently of one another, are hydroxyl or protected hydroxyl, with a compound of the formula,

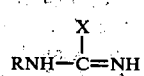

wherein
R has the same meaning as defined above;
X is amino, amino substituted by R as defined above or $C_{1-4}$ alkylthio;
and removing the hydroxyl protecting groups of the resulting compound when such protective groups remain.

2. A method according to claim 1, wherein
R is phenyl or phenyl substituted on the ring by halogen, $C_{1-4}$ alkyl, $C_{1-4}$ alkoxyl, carbamoyl, lower alkyl carbamoyl, phenylcarbamoyl, morpholinocarbamoyl or piperidinocarbamoyl.

3. A method according to claim 1, wherein X is amino or amino substituted with the group R wherein R is as defined in claim 1.

4. A method according to claim 1, wherein the reaction is conducted in the presence of a compound of the formula

wherein R is as defined in claim 1.

5. A method according to claim 1, wherein the reaction is conducted at atmospheric pressure.

6. A method according to claim 1, wherein R is unsubstituted phenyl.

7. A method according to claim 1, wherein X is amino.

8. A method for producing a compound of the formula

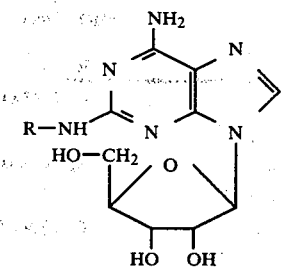

wherein
R is phenyl or phenyl substituted on the ring by halogen, $C_{1-4}$ alkyl, $C_{1-4}$ alkoxyl, carbamoyl, lower alkyl carbamoyl, phenyl carbamoyl, morpholinocarbamoyl, piperidinocarbamoyl, or $C_{2-5}$ alkanoyl;
or an acid addition salt thereof, which consists of protecting the hydroxyl groups of 5-amino-1-β-D-ribofuranosylimidazole-4-carboxamide, dehydrating the resulting hydroxyl-protected compound to yield a compound of the formula

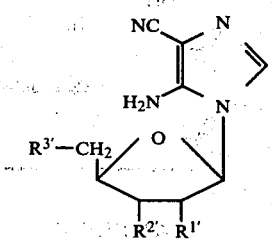

wherein
$R^{1'}$, $R^{2'}$ and $R^{3'}$, independently of one another, are protected hydroxyl, reacting the last mentioned compound with a compound of the formula

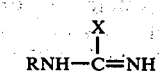

wherein
R has the same meaning as defined above, and
X is amino, amino substituted by R as defined above, or $C_1$-$C_4$ alkylthio; either after or without prior removal of the protecting groups, and removing the hydroxyl protecting groups of the resulting compound when the protective groups on the hydroxyls remain.

9. A method according to claim 8, wherein R is unsubstituted phenyl.

10. A method according to claim 8, wherein the hydroxyls of 5-amino-1-β-D-ribofuranosylimidazole-4-carboxamide are protected by a carboxylic acid-derived acyl group before the dehydration.

11. A method according to claim 8, wherein X is amino.

12. A method according to claim 8, wherein the reaction is conducted in the presence of a compound of the formula

R—NH$_2$ wherein R is as defined in claim 8.

13. A method according to claim 10, wherein the carboxylic acid-derived acyl is propionyl.

14. A method according to claim 8, wherein 5-amino-1-β-D-ribofuranosylimidazole-4-carboxamide is reacted with a reactive derivative of propionic acid, the resulting 5-amino-1-(2,3,5-tri-O-propionyl-β-D-ribofuranosyl)-imidazole-4-carboxamide is dehydrated, the resulting 5-amino-1-(2,3,5-tri-O-propionyl-β-D-ribofuranosyl)imidazole-4-carbonitrile is treated to remove the propionyls to yield 5-amino-1-β-D-ribofuranosylimidazole-4-carbonitrile and the last mentioned compound is reacted with phenylguanidine in the presence of aniline to produce N$^2$-phenyl-2,6-diaminonebularine.

15. A method according to claim 1, wherein R is phenyl which is substituted with C$_{2-5}$ alkanoyl.

16. A method according to claim 8, wherein R is phenyl which is substituted with C$_{2-5}$ alkanoyl.